United States Patent [19]

Schweikard

[11] Patent Number: 5,458,125
[45] Date of Patent: Oct. 17, 1995

[54] TREATMENT PLANNING METHOD AND APPARATUS FOR RADIOSURGERY AND RADIATION THERAPY

[75] Inventor: Achim Schweikard, Palo Alto, Calif.

[73] Assignee: Board of Directors of The Leland Standford Jr. University, Palo Alto, Calif.

[21] Appl. No.: 188,436

[22] Filed: Jan. 28, 1994

[51] Int. Cl.⁶ .................................................. A61B 6/00
[52] U.S. Cl. ........................ 128/653.1; 606/130; 378/65; 364/578
[58] Field of Search ........................ 128/653.1; 606/130; 364/413.26, 578; 378/65

[56] References Cited

U.S. PATENT DOCUMENTS

| | | | |
|---|---|---|---|
| 3,987,281 | 10/1976 | Hodes | 364/413.26 |
| 5,027,818 | 7/1991 | Bova et al. | 128/653.1 |
| 5,205,289 | 4/1993 | Hardy et al. | 128/653.1 |
| 5,291,404 | 3/1994 | Kurokawa et al. | 364/413.26 |
| 5,341,292 | 8/1994 | Zamenhof | 364/413.26 |

*Primary Examiner*—Ruth S. Smith
*Attorney, Agent, or Firm*—Medlen & Carroll

[57] ABSTRACT

Disclosed is a method and system for inverse planning of radiosurgery of tumors. Isocenter points are replaced systematically throughout a model of a tumor to generate a sequence of simulated radiation beams. This crossing geometry and intersection pattern of these beams is then computed. Through fine tuning of certain variables used in the calculations in accordance with the present invention, radiosurgery is planned in a manner which avoids over irradiation of healthy tissue and critical regions, and allows for homogeneity of dose inside the tumor. The method of the present invention allows for exact decision about the feasibility of use-defined dose distributions.

31 Claims, 13 Drawing Sheets

FIG. 6
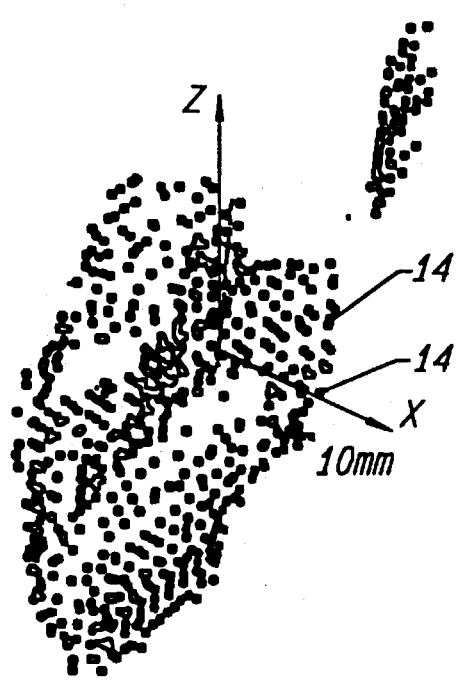
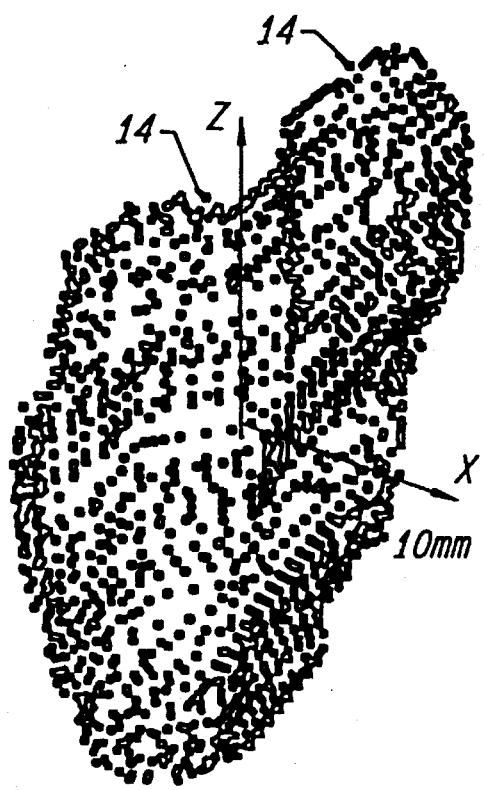
FIG. 8
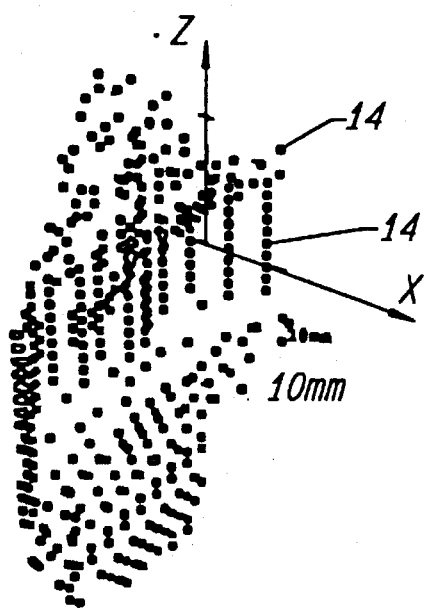
FIG. 7

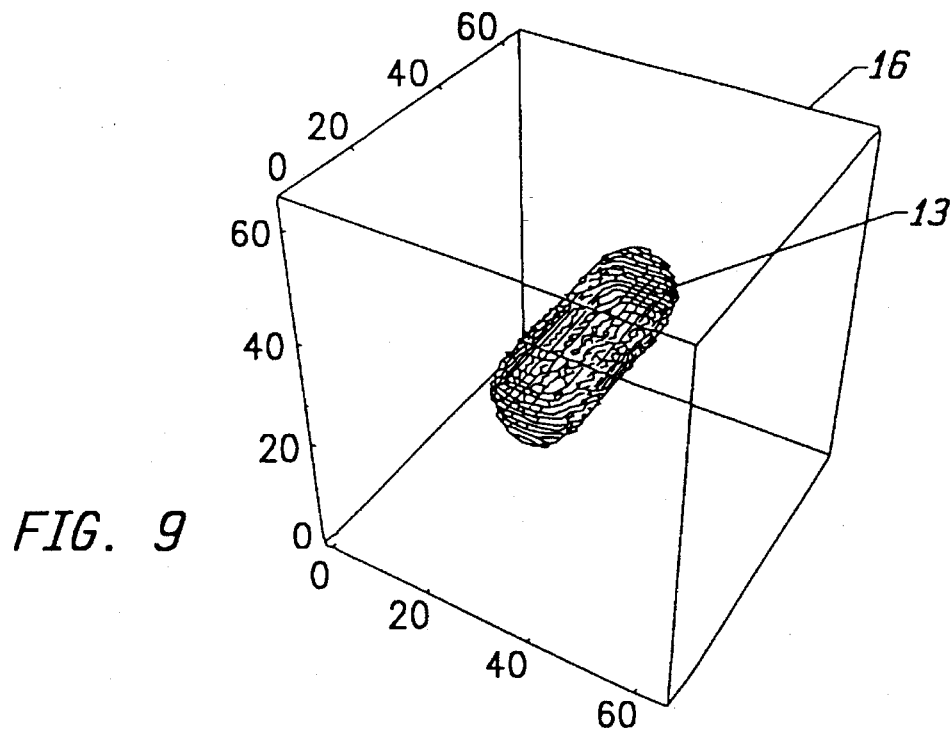
FIG. 9
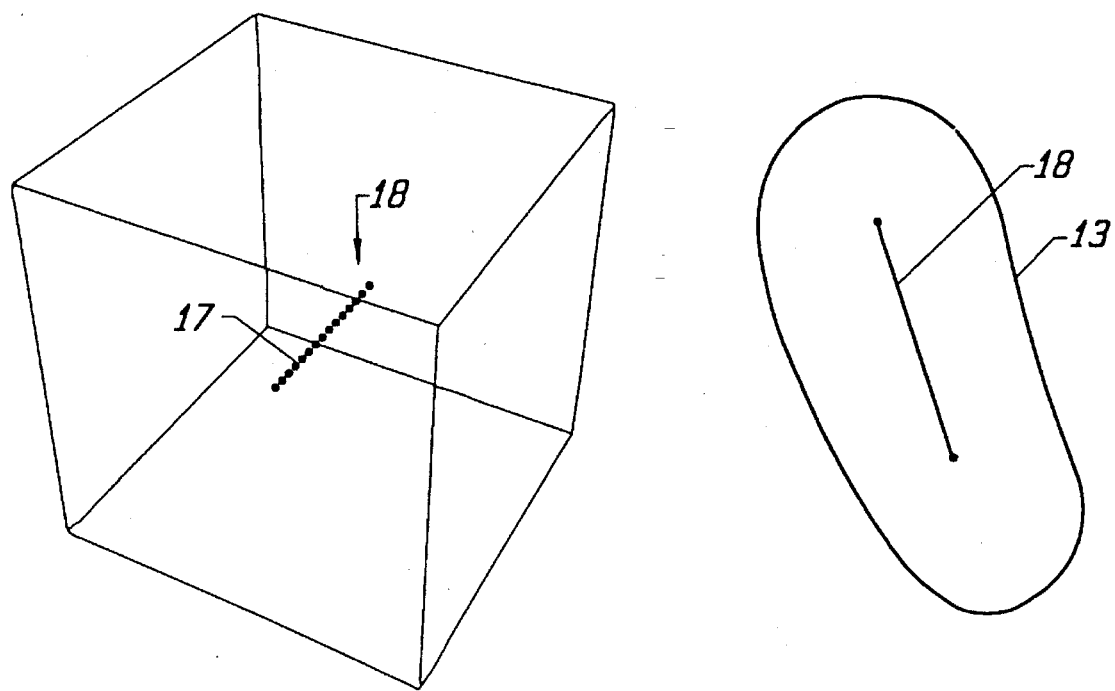
FIG. 10
FIG. 11

FIG. 22A    FIG. 22B    FIG. 22C
FIG. 22D    FIG. 22E    FIG. 22F
FIG. 22G    FIG. 22H    FIG. 22I
FIG. 22J    FIG. 22K    FIG. 22L
FIG. 22M    FIG. 22N    FIG. 22O

TREATMENT PLANNING METHOD AND APPARATUS FOR RADIOSURGERY AND RADIATION THERAPY

BRIEF DESCRIPTION OF THE INVENTION

The present invention relates to radiosurgery and more particularly to an apparatus and method for treatment planning for radiosurgical operations.

BACKGROUND OF THE INVENTION

In radiosurgery, brain tumors (and other real formations) are destroyed by an intense beam of radiation. A necrotic dose is delivered to a tumor by cross-firing from multiple directions, in order to reduce the amount of energy deposited in healthy tissue. Hence, unlike with more invasive surgery, tissue surrounding the tumor can be protected to some extent. Although radiosurgery has been in use for several years, high ablative accuracy has only recently been made possible by progress in focused radiation sources and imaging techniques. With a risk that is proportional to both dose and the volume irradiated, radiation necrosis of tissue adjacent to a treated lesion remains the major complication of stereotaxic radiosurgery. Concerns remain as to whether particular volumes of tissue receive too much or too little radiation according to the prescription for treatment.

The radiosurgical treatment consists-of several phases. First, a precise three-dimensional (3D) map of the anatomical structures in the area of interest (for example, the brain) is constructed using computed tomography (CT) and magnetic resonance (MR) techniques. Next, a motion path for the radiation beam is computed to deliver a dose distribution that the surgeon finds acceptable (taking into account a variety of medical constraints). Finally, a jointed mechanism moves the radiation source according to this path.

A collimated radiation source is positioned in a sequence calculated to localize the energy deposition into a volume that as closely as possible conforms to that requiring treatment, while avoiding exposure of nearby healthy tissue. A system and method for performing stereotaxic surgery is disclosed in U.S. Pat. No. 5,207,223 issued to Adler on May 4, 1993 and in U.S. patent application Ser. No. 07/989,045, which is a continuation-in-part application of issued U.S. Pat. No. 5,207,223 which are incorporated by reference herein. The forward dosimetry problem is to compute the dose distribution in a tissue given a treatment plan. The inverse dosimetry problem is to find a treatment plan whose execution will achieve a desired dose distribution. Issues related to planning are not discussed in the above discussed patent or patent application. The planning methods of the present invention rely on a system with general kinematics such as the Neurotron-1000 such which is described in the above mentioned patent and patent application.

The dose distribution is an important parameter is radiosurgery. Whether fixed or frameless stereotaxic radiosurgery is used, it is important to plan a particular scheme for the application of radiation beams to the tissue. By providing dose distribution within the prescribed limits, treatment would be optimized and damage to healthy tissue would be minimized. It is thus desirable to find a suitable motion for the beam given the shape and the location of the tumor.

SUMMARY OF THE INVENTION

A treatment planning method and system for radiosurgery including an apparatus providing up to six degrees of freedom, allows full kinematic flexibility for manipulation of the radiation beam, and thus, the beam can cross-fire from all directions at the tumor during treatment. A three-dimensional map of the anatomical structures in the area of interest is generated. The reverse planning method and system of the present invention further includes generating a sequence of beam configurations (positions and orientations) and radiation dose weights for achieving the specified distribution, particularly for non-spherical shapes. The beam dose weighing of the present invention is particularly appropriate for radiation therapy as well.

In order to form targets for the beam, isocenter points are generated. Several different isocenter generation methods are used. For example, a line of isocenters is formed, following the curvature of the tumor. If the tumor is cigar-shaped, the isocenters are distributed along a straight line. If the tumor is banana shaped, the isocenters points are distributed along a line segment or a sequence of several line segments. The line segments are specified by endpoints, which can be moved in the same way as single isocenters. Typically, the same collimator radius is used for the entire segment. If the tumor is banana, horseshoe or doughnut shaped, the line segment will be bent. Moreover, a grid of isocenter points is imposed on the tumor shape.

The beam's position and orientation is provided with respect to each isocenter point. The dose distribution is provided by a method and system for determining the weight of each individual beam from constraints which are assigned by the surgeon. The radiosurgical treatment planning method and system of the present invention includes the steps of and means for mapping a volume of tumorous tissue requiring irradiation and its surrounding regions to generate a model; distinguishing between tumorous tissue regions of the model and other regions requiring less than a predetermined dose of radiation; positioning isocenter points in a distributed manner within said model of said mapped tumorous tissue requiring irradiation; simulating radiation beams passing through the isocenter points; and determining which regions of the tumorous tissue received the predetermined dose of radiation.

BRIEF DESCRIPTION OF THE DRAWINGS

FIG. 6 shows the grid of FIG. 5 retracted;

FIG. 7 shows the grid of FIG. 5 further reduced;

FIG. 8 shows the grid of FIG. 5 expanded;

FIG. 9 shows another isodosic surface for a tumor of box-like shape;

FIG. 10 shows a line segment of isocenter points evenly spaced on this segment;

FIG. 11 shows a different tumor shape with an isocenter line segment;

FIG. 22 shows a photographic film phantom.

DETAILED DESCRIPTION OF THE INVENTION

Figure 1:
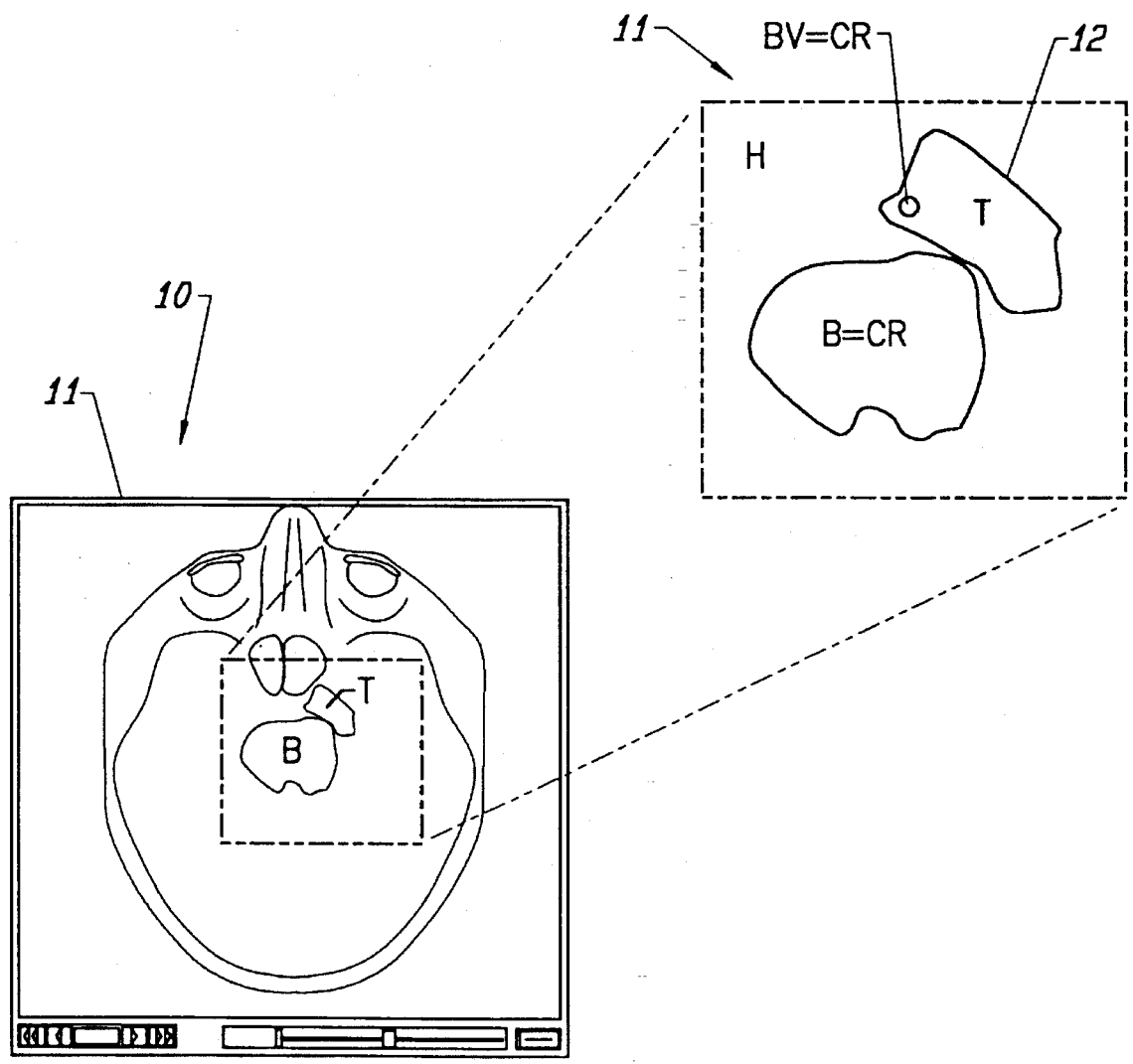
FIG. 1 shows a computer screen image of a slice of a CT scan with an enlargement of the area of interest.

As discussed above, a scan is made of the tumorous tissue region. These images are made up of two dimensional images of the tissue region which when compiled, can be modeled as a three-dimensional image. FIG. 1 shows a computer screen display of an image of a scanned tumorous tissue region 10. Box 11, which surrounds the area of interest, is expanded above and to the right of the computer screen shown in FIG. 1. Tissue is labeled, taking into account the levels of radiation which should be administered to the tissue in order to provide effective treatment of the tumor. The tumor is shown as "T" and referred to as numeral 12. In this scan, the tumor is shown as surrounding a blood vessel "BV" which is a critical region, "CR". Moreover, the tumor abuts the brainstem, "B" which is also a critical region, "OR". The tumor is in turn surrounded by healthy tissue, "H". During treatment, the beam is moved to allow for an even distribution of radiation dose in healthy tissue as well as in the tumor. For effective surgery, radiation in region T should be maximized but radiation to regions "OR" should be avoided and radiation to regions H should be minimized. The method and apparatus of the present invention provides the ability to plan and treat different sections of the region of interest in box 11 with different levels of radiation. According to the present invention, a sequence of beam configurations (positions and orientations) and dose weights for achieving the specified distribution is provided given a representation of anatomical structures and constraints on the dose to be absorbed by each structure, such as that shown in FIG. 1. The constraints are predetermined values imposed by a user of the present invention:

Radiation beam configurations are imposed on the tumor region by either one or both methods provided by the present invention. An isocenter point is a point in space where several radiation beams converge. Thus, several (cylinders) beams are arranged in space in such a way that their axes cross at the isocenter point.

The present invention provides methods for distributing isocenter points in space in such a way that a given (often non-spherical) tumor region receives high radiation dose, and that the tissue surrounding the tumor will receive low dose. As will be described in more detail, isocenters are formed through computer simulations, by either generating a tumor region surface and imposing the isocenters on that surface or by forming a line segment which follows the curvature of the tumor region within the interior of the tumor region.

Figure 2:
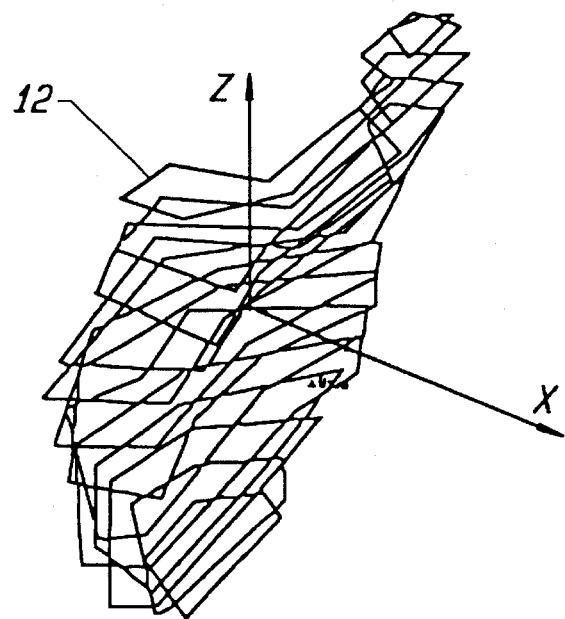
FIG. 2 shows a three-dimensional image constructed of polygonal outlines of a plurality of CT scan slices such as that shown in FIG. 1.

Regarding the surface method of the present invention, FIG. 2 shows a plurality of two dimensional outlines of the tissue region which when compiled, form an image of a three dimensional model or an anatomical map. The images show for example, axial, sagittal, or coronal cross-sections of the brain. Typically, each two-dimensional outline is similar to that shown as polygon shape 12 of FIG. 1. These polygons are thickened between two cross-sections. The polygons delineating the anatomical structures such as the tumor and the critical regions can either be computer generated or hand drawn. The outlines shown in FIG. 2 have been generated by drawing polygonal shapes around the tumor region shown in the two dimensional scan image to most closely approximate the shape of the regions. In FIG. 2, the model is shown mapped according to a three dimensional XYZ coordinate system. For simplicity, FIG. 2 shows only a tumor region, however, below mapping of both a tumor and critical region are discussed.

Figure 4:
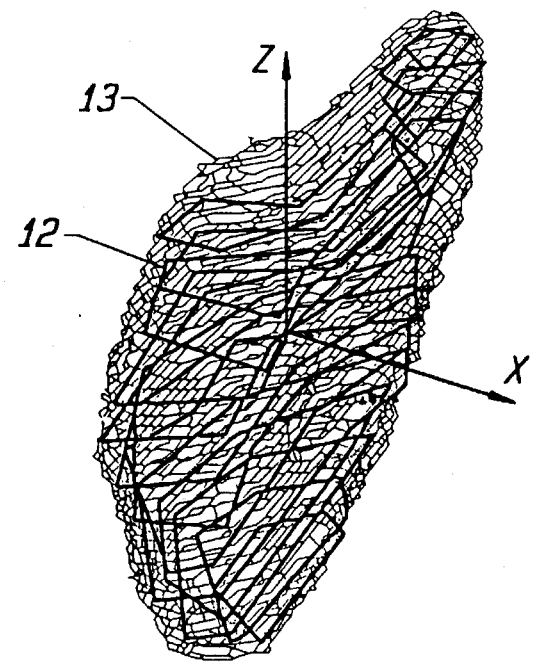
FIG. 4 shows the surface of FIG. 3 superimposed on the polygonal image shown in FIG. 2.
Figure 3:
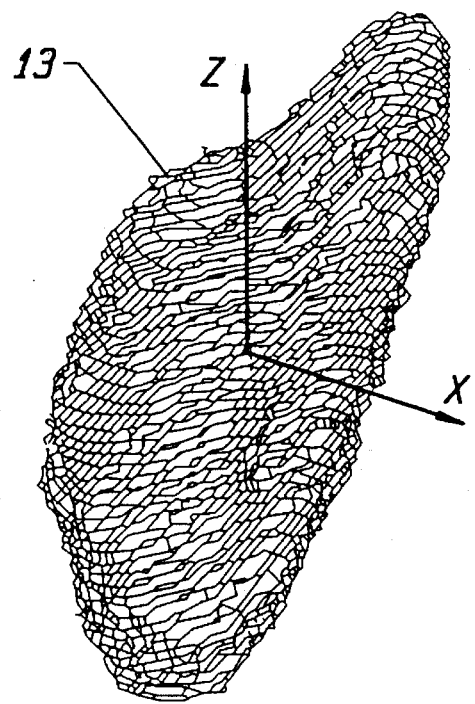
FIG. 3 shows an isodosic surface.

FIG. 3 shows the isodosic surface 13 alone without the slices shown in FIG. 2. That is, FIG. 3 shows the region receiving 50% or more of a radiation dose after the planning method of the present invention is used. Turning to FIG. 4, the surface 13 is superimposed upon the image formed by the polygons of FIG. 2, thus showing that the isodosic surface and the polygons are well matched, In the same way, a surface representing a critical region or healthy tissue can also be generated.

Figure 5:
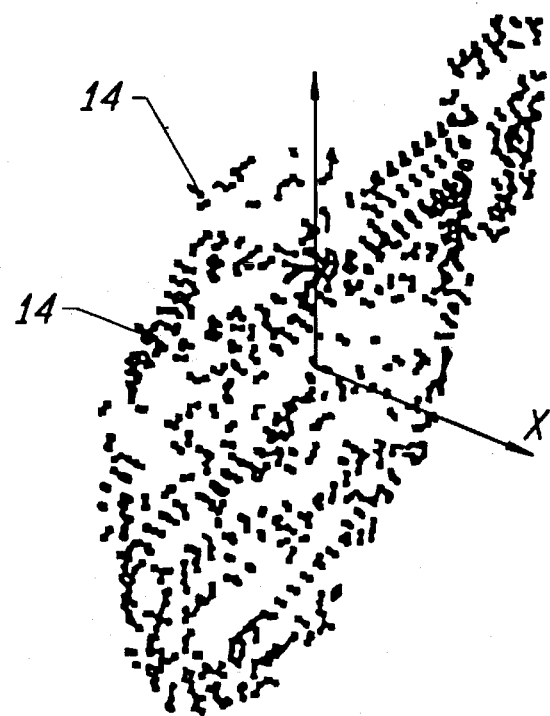
FIG. 5 shows a grid of isocenter points superimposed on the surface in FIG. 4.

According to the present invention as shown in FIG. 5, plurality of isocenter points 14 are positioned in a distributed manner on the surface of the model of FIGS. 3 and 4. Under this embodiment, a grid of distributed points forms a plurality of isocenters. The points shown are evenly distributed, however, some arrangement different from even distribution is also within the scope of the present invention. For example, the grid can be formed of a pattern of points which are not necessarily evenly distributed.

Alternatively, the grid can be a three-dimensional grid wherein some of the points are positioned both on the surface of the volume and within the volume. Also, points of the grid can be positioned only in the interior of the volume so that they form a plurality of isocenters to which beams are directed. In any event, the isocenter points shown in FIG. 5 are positioned in a distributed manner so that they are superimposed upon the model of FIG. 3.

It is possible to change the positioning of the isocenter points 14 in several different ways. For example, as shown in FIGS. 6–8, the surface grid can be retracted or expanded. FIG. 6 shows a number of points on the surface grid of FIG. 5 reduced by a factor fixed to be specified by the user. The method of the present invention provides the ability to retract or expand the surface isocenters. One method for doing so is by assigning those points on a regular grid in space, voxels, which are inside the tumor region a label "1". All voxels outside the tumor region are labelled "0". To retract or shrink the isocenter surface, the labels of all points with a neighbor labelled "0" are changed to "0". Similarly, to expand the isocenter surface, voxels labelled "0" having a neighbor labelled "1" are re-labelled "1". FIG. 7 shows the number of points on the surface grid reduced by a factor of four by the same method. On the other hand, referring to FIG. 8, the number of points of the grid of isocenter of points are expanded by a factor of two. In an alternative embodiment, the number of points 14 of the grid remains the same but the grid itself is caused to contract or expand, thus causing the grid to become more or less dense.

A second manner in which to generate isocenter points is to draw a line segment or sequence of line segments following the curvature of the tumor. Isocenter points are then placed along that segment or segment sequence by the system. This will result in a box-shaped or banana-shaped region of high dose. Using a computer having a click-mouse, the segment sequence is drawn by clicking at end points. For example, if the tumor is cigar shaped as that shown in FIG. 9, or having a shape as that shown in FIG. 11, the line segment 18 is a straight line. If the tumor is banana shaped (not shown), a sequence of segments are used. The line segment mode can be visualized as pulling or stretching a single isocenter treatment. An elongated region receives a high dose, and allows for a sharp dose drop-off around that region.

Depending upon the circumstances, the user of the present invention may choose to use the grid approach as shown in FIGS. 5–8 or may use the line segment approach shown in FIGS. 9–11, or both. After positioning the plurality of isocenter points so that they can be superimposed on the generated model, radiation beams passing through the isocenter points are simulated by any suitable computer means. Thus, the resulting distribution is calculated, and displayed, assuming all beams have the same weight. After display, the surgeon may choose to change isocenter point placement or beam directions. In the following step, individual weights are assigned to the beams thus chosen.

Figure 12:
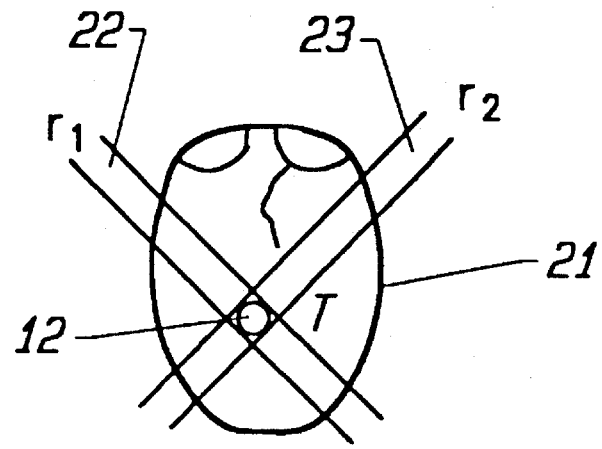
FIG. 12 depicts a skull having a tumor region with two beams passing therethrough.
Figure 13:
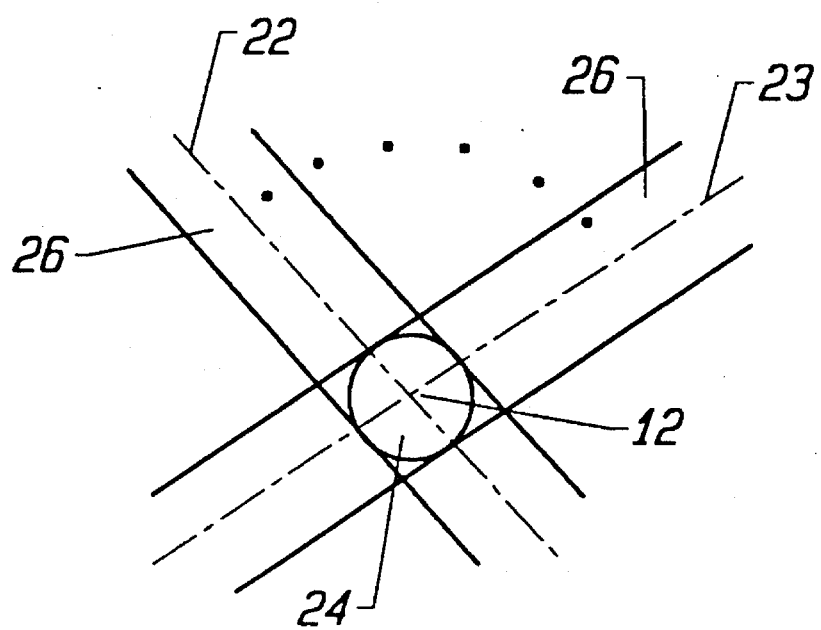
FIG. 13 illustrates a close up of the tumor region of FIG. 12.

Referring to FIG. 12, a skull 21 having a generally spherical tumorous region 12 is depicted as receiving two beams 22 and 23. Typically, while more than two beams will pass through a single tumor region 12, however, for illustrative purposes, the most simple case is shown. Turning to FIG. 13, there it is shown that each beam's axis passes through the isocenter of the region 12. The region where the beams paths cross, region 24, receives the highest radiation dose. The regions where the beams paths do not cross, regions 26, receive lower radiation dose.

Figure 14:
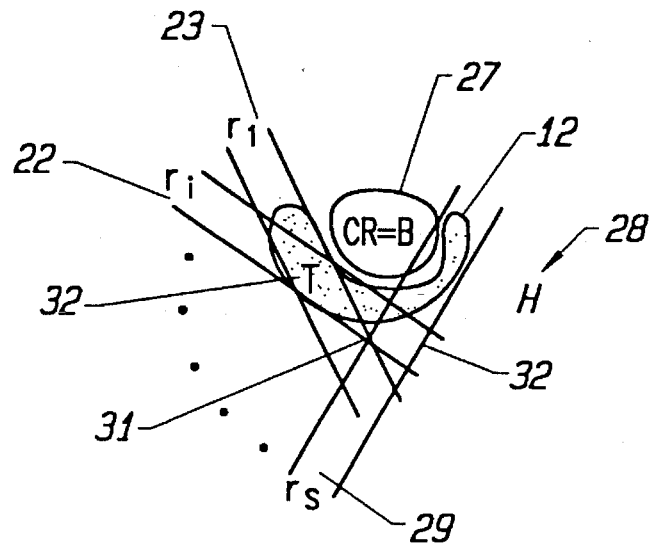
FIG. 14 depicts a tumor shape surrounding a brain stem shape and beams passing therethrough.
Figure 15:
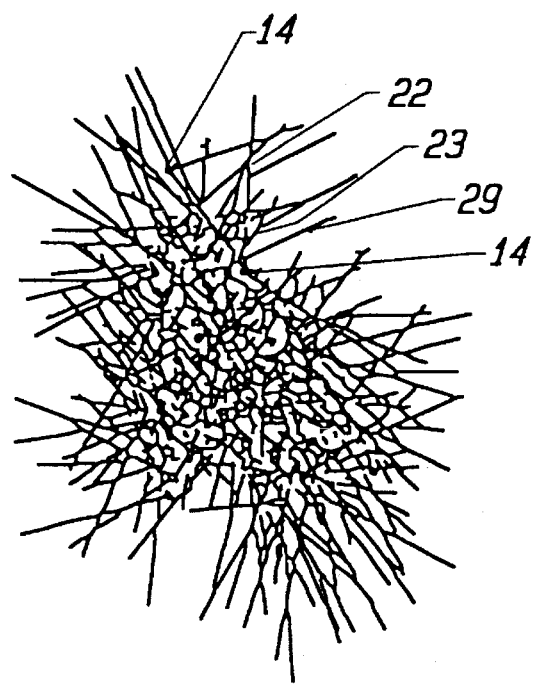
FIG. 15 shows another tumor shape with beams passing therethrough.

While FIG. 13 shows a spherically shaped tumor region 12, the present invention provides the ability to treat non-spherically shaped tumors as shown in FIGS. 14 and 15. As discussed with respect FIG. 1, tumor region 12 abuts the brainstem, B, which is also referred generally as a critical region, CR, indicated by reference numeral 27. Healthy tissue 28 surrounds both the critical region 27 and the tumor region 12. Thus, several different radiation requirements are present in this situation. The tumor 12 of course must have a radiation dose sufficient to cause the tumor to be adequately treated. Moreover, it is important to avoid elevated dose of radiation to the a critical region 27. Critical regions are optical nerves, blood vessels such as a carotid artery, optic chiasm, the eyes or other structures defined by the user. Thus in order to treat tumors near critical areas requires that the treating physician identify the maximum radiation dosage allowed to be present in a critical region 27 and the minimum dosage required in the tumor region 12. FIG. 14 further shows three beams passing through the tumor region. The region 31 in which the paths of beams 22, 23 and 29 intersect receives the highest dosage of radiation, while regions 32 in which only two paths intersect receive a lesser dose.

In the reverse dosimetry of the present invention, beam paths are computed to generate a desired dose distribution. Beam paths are planned for the varied shapes and relative locations of tumorous structures. According to a system of the present invention, a dosimetry program simulates treatment and computes the dose distribution which is generated by this treatment. Graphical tools are provided to display 3D anatomical maps and cross sections, visualize dosimetry results, and simulate robot motion.

Beam position and orientation selection is performed according to a generating sequence. For example, using a random beam generator, a beam configuration passing through a grid as shown in FIGS. 5–8 results in a beam selection such as that shown in FIG. 15 is generated. Were a surgeon to specify a line segment as the isocenter points as shown in FIGS. 10 & 11, the tumor center would absorb a much higher dose than points on the tumor surface. Placing isocenter points on the tumor surface avoids this drawback, but usually yields a slightly less sharp dose drop-off around the tumor.

Figure 16:
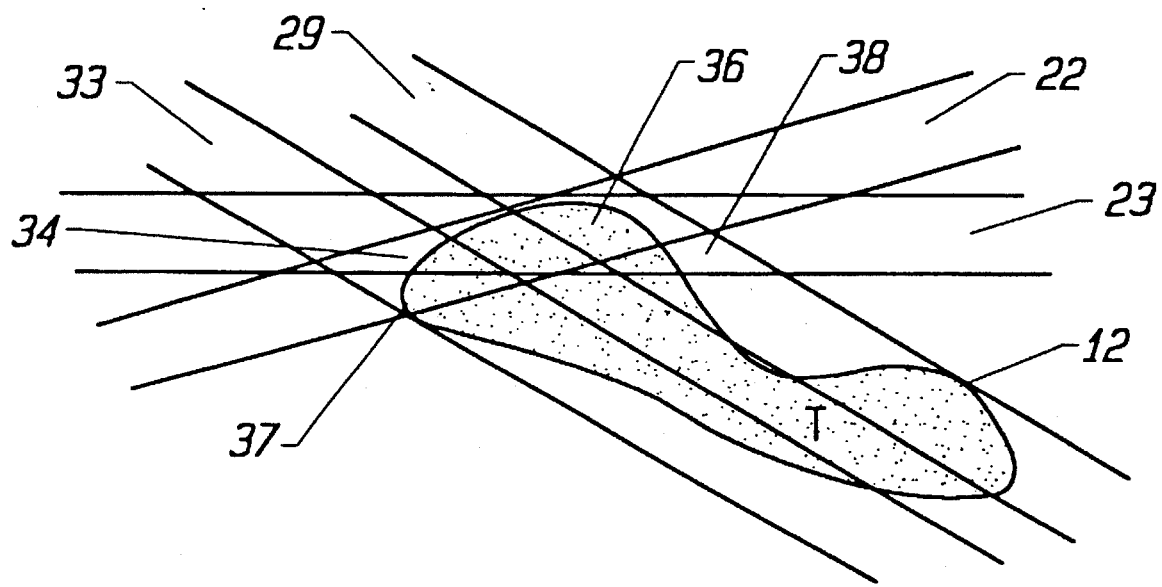
FIG. 16 cell formation by intersection simulated beams according to the present invention.

In FIG. 16, four beams 22, 23, 29 and 33 cross each others paths in several locations. At locations 34 and 36 cells are formed where three beams cross. The system of the present invention keeps an internal representation of all beams crossing critical regions and tumor regions. After each weight change, the resulting dose distribution is computed and displayed.

During a simulation of treatment, the simulated six degrees of freedom arm moves in point-to-point mode through a series of configurations. At each configuration, the beam is activated for a small time interval, $\delta t$, while the arm is held still. The intensity of the beam is constant, hence $\delta t$ determines the dose delivered at each configuration. This duration can vary from one configuration to the next but is upper-bounded for patient protection. In order to achieve an appropriate dose distribution within reasonable time, the beam is activated at a series of 300 to 400 configurations. Currently, the beam has a circular cross-section the radius of which remains constant throughout the same operation. However, this radius initially can be set between 5 mm and 40 mm by selecting an appropriate collimator for focusing the beam. In the future, variable multi-leaf or slot collimator will allow the generation of beams with non-circular cross-sections.

Figure 18:
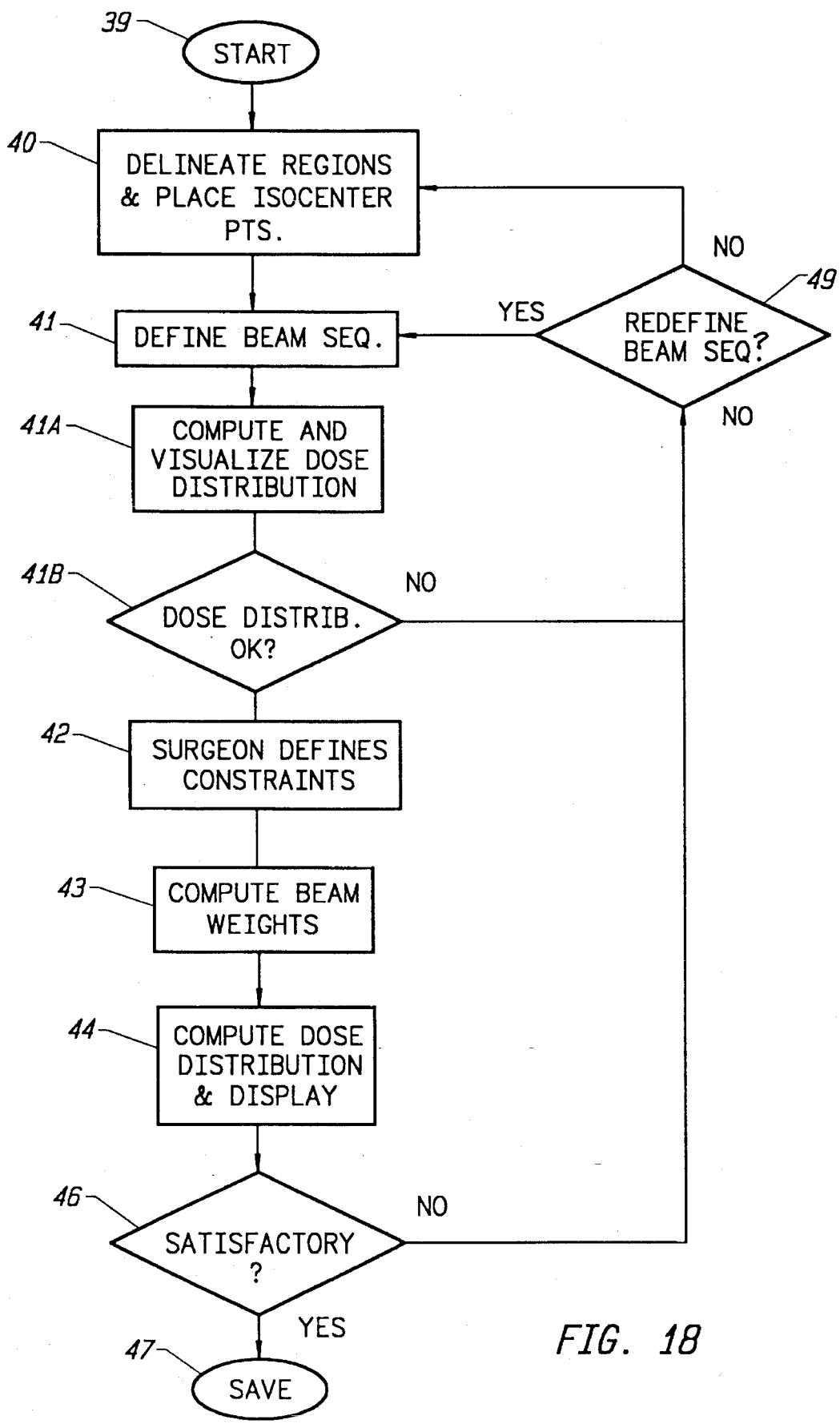
FIG. 18 shows a flow chart according to the present invention.

According to the flow chart of FIG. 18, the surgeon starts at step 39, delineates the regions and/or places the isocenter points at step 40. The system generates the radiation beam sequence at step 41. At Step 41A, the system computes the dose distribution resulting from those beams from even weights and displays the result on the screen display (see FIG. 20 below). The surgeon is then asked if this distribution is satisfactory in Step 41B. If not, delineation, isocenters, the number of beams, and other input parameters can be changed by returning to Step 40. After satisfactory results are obtained, the surgeon defines constraints for dose in different regions at Step 42. In one embodiment, the beam is simulated as a cylinder of fixed radius with constant fluence. The radius r of this cylinder and the number n of beam configurations to consider are given as input.

Figure 19:
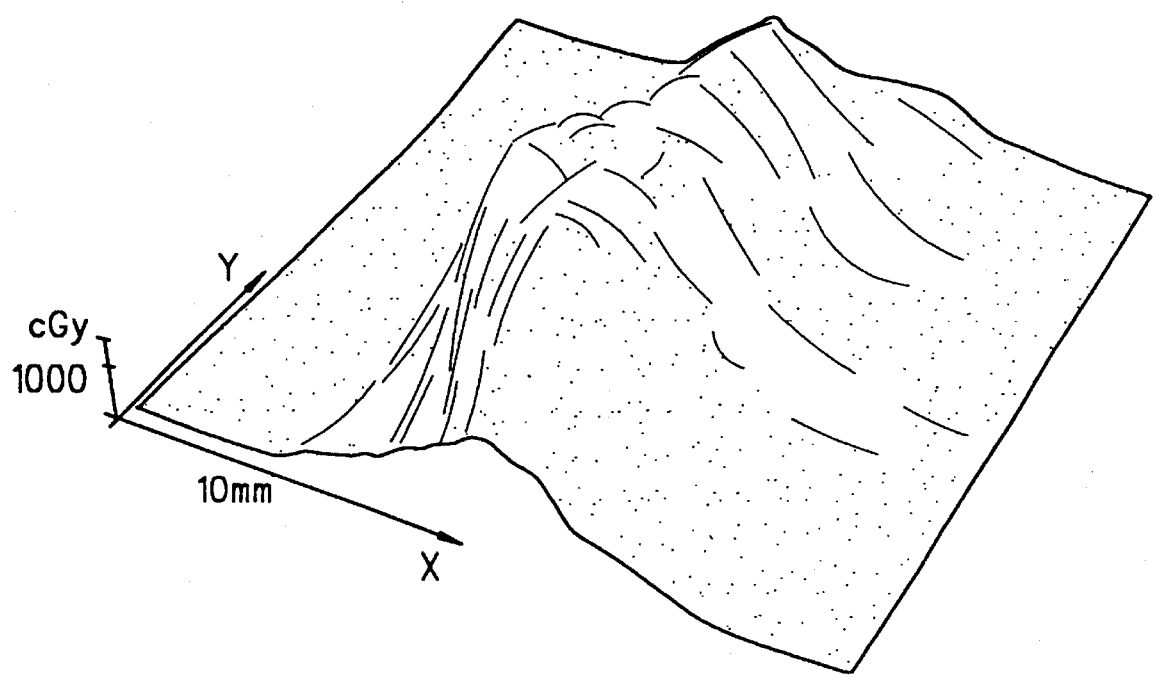
FIG. 19 is a display of the dosimetric results in a cross section of the tumor region.

After computing the beam sequence at step 43, the direct dosimetry program is called to compute the dose distribution at step 46. Three types of graphical visualization are available to the surgeon for evaluating a treatment plan. First, an isodosic surface in 3D is provided, that is, an surface that bounds the region that receives a dose greater than some specified value (see FIG. 3). In the alternative, a gray-level representation and isodosic curves in planar cross-sections is provided. Further alternatively, dose-volume histograms (DVH) showing the volume (ordinate values) absorbing a dose x as a function of x (abscissa values). A separate DVH is computed for the tumor, critical tissue, and for tissue surrounding the tumor. FIG. 19 is a display of the dosimetric results where of a cross section of the tumor region.

The program questions whether the result from Step 44 is satisfactory. If not, steps are repeated through discussion box 49. When the surgeon finds a result from step 44 satisfactory, the treatment plan can be saved at step 47. The process can be started again at step 39, starting with entirely new parameters or previously used parameters can be used as well. The surgeon can interactively try different techniques to generate beam configurations. For example, for the same set of model and beam sequence configurations, different values of $\beta$, yield different values of $\alpha$. Smaller values of $\beta$ give larger values of $\alpha$. However, large values of $\beta$ lead healthy tissue close to the tumor to absorb higher doses.

Thus, if the surgeon does not find the results from step 44 satisfactory, step 48 questions whether to redefine constraints. If the answer is yes, the previously used region model 40 and beam sequence 41 will be used to compute the beam weights with new surgeon defined constraints. If the answer is no, then the planner will choose whether to redefine the beam sequence at step 49. If the surgeon chooses to redefine the beam sequence, the beam sequence is redefined at step 41. If the surgeon chooses not to redefine the beam sequence, then the region is remodeled at step 40. Accordingly, the principle of the planning method of the present invention is that beams are selected given the input tumor shape, the resulting dose distribution (assuming even weight for all beams) is computed and visualized on a computer display screen. If the surgeon finds the distribution acceptable, the beams are then weighted. The resulting distribution is displayed so that the surgeon can return to any of the previous steps, modifying input parameters.

It is assumed that the n beam configurations have already been determined, and that the focus is on determining how they should be weighted. Also it is also assumed that the radiation beam is generated by a circular collimator of given radius r.

Let $C_1, \ldots, C_n$ denote the cylinder beams at the n selected configurations. A dose value $\omega_i \geq 0$ is computed for every $C_i$. The values $\omega_1, \ldots, \omega_n$ determine a dose distribution D. D is defined as follows. If p is a point and $C_{i1}, \ldots, C_{ix}$ are the cylinders containing p, then $D(p) = \omega_{i1} + \ldots + \omega_{ix}$. (This definition gives a coarse model of photon beam characteristics. Refinements described below allow for a more accurate representation of these characteristics.)

Two disjoint regions T (for tumor) and H (for healthy tissue), with the following constraints are considered: the dose delivered at each point in T must be larger than some value $\alpha$, while the dose at each point of H must be below $\beta (\beta < \alpha)$. The n cylinders, T, and H define an arrangement of cells in space. Each cell is defined as a maximal connected set not containing any piece of the boundaries of regions T and H or the cylinders. For each cell a label is computed. A cell x in cylinders $C_{i1}, \ldots, C_{ix}$ has label $I = \{i_1, \ldots, i_x\}$.

The calculation of $\omega_1, \ldots, \omega_n$ reduces to finding a point in the intersection of two n-dimensional polyhedral sets: If x is in T and labeled by $\{i_1, \ldots, i_x\}$ then x determines the inequality:

$\alpha \leq \omega_{i1} + \ldots + \omega_{ix}$,

A cell x, labeled by $\{i_1, \ldots i_x\}$ in H gives:

$\beta \geq \omega_{i1} + \ldots + \omega_{ix}$.

The inequalities for all cells in T determine a convex polyhedral set $P_\alpha$. Similarly, the inequalities derived from the cells in H determine a polyhedron $P_\beta$. If $P_\alpha$ and $P_\beta$ intersect, any point $(\omega_1, \ldots, \omega_n)$ in the intersection gives a dose distribution that satisfies the given constraints. Otherwise the problem admits no solution.

More generally, several healthy critical or non-critical regions $H_1, \ldots, H_q$ are specified and marked by distinct maximal doses $\beta_1, \ldots, \beta_q$. Polyhedra $P_\alpha, P_{\beta i}, \ldots, P_{\beta q}$ are then obtained. Any point $(\omega_1, \ldots, \omega_n)$ in the intersection of these polyhedra determines a dose distribution that satisfies the input constraints.

The intersection of the polyhedral sets $P_\alpha, P_{\beta i}, \ldots, P_{\beta q}$ is another n-dimensional convex polyhedral set. Extreme points of this set can be computed, providing the ability to directly deal with some optimality criteria (e.g., in addition to satisfying the input constraints defined by $\alpha, \beta_1, \ldots, \beta_q$, minimize the dose delivered to some region $H_i$). A point in the intersection of the two or more polyhedra is computed with linear programming algorithms.

The number of cells and thus the number of inequalities is reduced by only using minimal or maximal cells. Consider two inequalities derived from two cells x and x' in T. Let $L = \{i_1, \ldots, i_x\}$ and $L' = \{i_1, \ldots, i_{x'}\}$ be the labels of x and x'. If $L \subset L'$, then the inequality given by x implies the inequality given by x', since all $\omega_i$ are positive or null. A T-cell is called minimal, if its label is not a superset of any other T-label. Similarly, a cell in $H_i$ is called maximal, if its label is not a subset of any other label in $H_i$. Thus, in the above polyhedral intersection test, only minimal T-cells and maximal H-cells need to be considered.

Assuming that T and $H_1, \ldots, H_q$ have constant complexity, the total arrangement above also has $\Theta(n^3)$ cells. These cells, the associated inequalities, and the adjacency relationships between cells can be computed in nearly cubic time. In the inequality set, all inequalities for non-minimal T-cells, as well as inequalities for non-maximal cells in $H_i$ (separately for each i) can be deleted.

The above reduction can be done in time linear in the total number of cells: The cell arrangement is traversed in depth-first sequence. Between two adjacent cells x and x' in T a cylinder wall is traversed. If the wall is traversed from the interior to the exterior of the cylinder, then x is non-minimal, so we can delete its label. On the other hand, if the cylinder wall is traversed from the exterior to the interior, then the label of the new cell x' is removed. These relationships are reversed for pairs of adjacent cells in one of $H_i$.

Figure 17:
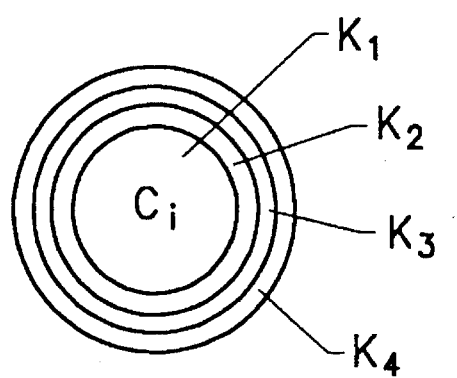
FIG. 17 depicts decreasing dose values in a cylindrical beam.

In reality the radiation beam does not behave exactly as a cylinder with constant fluence and thus the beam characteristics need to be approximated. The dose delivered by the beam decreases with distance to the beam's central axis. This decrease has been measured in clinical studies and can be represented by an exponential function. According to the method of the present invention, a more accurate model by representing a beam as a series of p concentric cylinders is obtained. In the inequalities, the variables for the added cylinders occur with decreasing coefficients as shown in FIG. 17.

The beam fluence also decreases with depth traveled in tissue. To represent this effect, the cylinders are divided by planes orthogonal to their central axis and are adapted the coefficients accordingly.

A third effect observed in measurements is the beam widening with distance from the source. This effect can be taken into account by using cones instead of cylinders.

In another embodiment of the weighing process, a fine regular 3D grid of points is placed across the brain map (here the grid resolution is 1 mm), wherein each grid point is labeled by the set of cylinders that contains it. The labels associated with the points in the tumor yield inequalities determining a polyhedron $P_\alpha$. Prior to collecting these inequalities, all grid points in the tumor representing non-minimal cells are removed.

A minimal value $\alpha$ is specified by the surgeon for the tumor region T. Additionally a common threshold $\beta$ is given for all beams, i.e., no beam can exceed $\beta$ in weight. (If no point in H is in more than x beams simultaneously, then it can be ensured that the dose in H remains below $x\beta$.)

Parameters $U_i$ are defined so that $\rho_\lambda = (U_1, \ldots, U_n)$ with $U_i = \lambda \beta$ if $C_i$ crosses a critical region, and $U_i = \beta$ otherwise for values $0 \leq \lambda \leq 1$. It is then tested whether $\rho_\lambda$ is in $P_\alpha$ for $\lambda = 1$. Intersecting the line segment $\{\rho_\lambda | 0 \leq \lambda \leq 1\}$ with the boundary of $P_\alpha$ gives the minimum value of $\lambda$ such that $\rho_\lambda$ is in $P_\alpha$. If there is no such value, then the answer to the question step 46 of the flow chart of FIG. 18 is no. Thus, either the beam directions or the value for $\beta$ must be adapted accordingly, or new beam directions should be generated and the process must be repeated until satisfactory results are provided.

A simplified scheme for beam weighing can be employed in the alternative to that discussed above. After the beams are selected, the subset of all beams through critical regions is computed. All the beams which do not pass through the critical regions can be assigned a weight of alpha. All of the beams crossing the critical regions are weighted with a value of beta. The user can then change alpha and beta and have the resulting distribution displayed interactively.

Figure 20A:
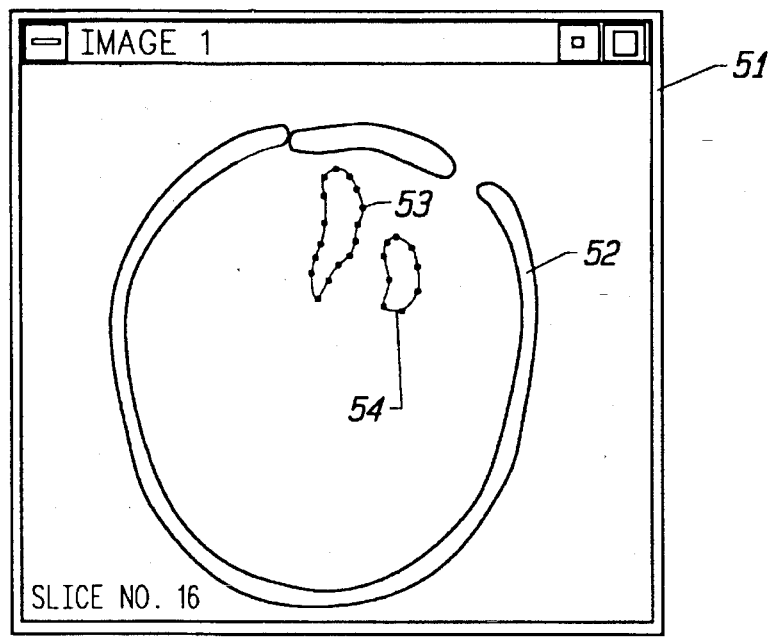
FIGS. 20A and 20B depict an embodiment of a computer screen display according to the present invention.
Figure 20B:
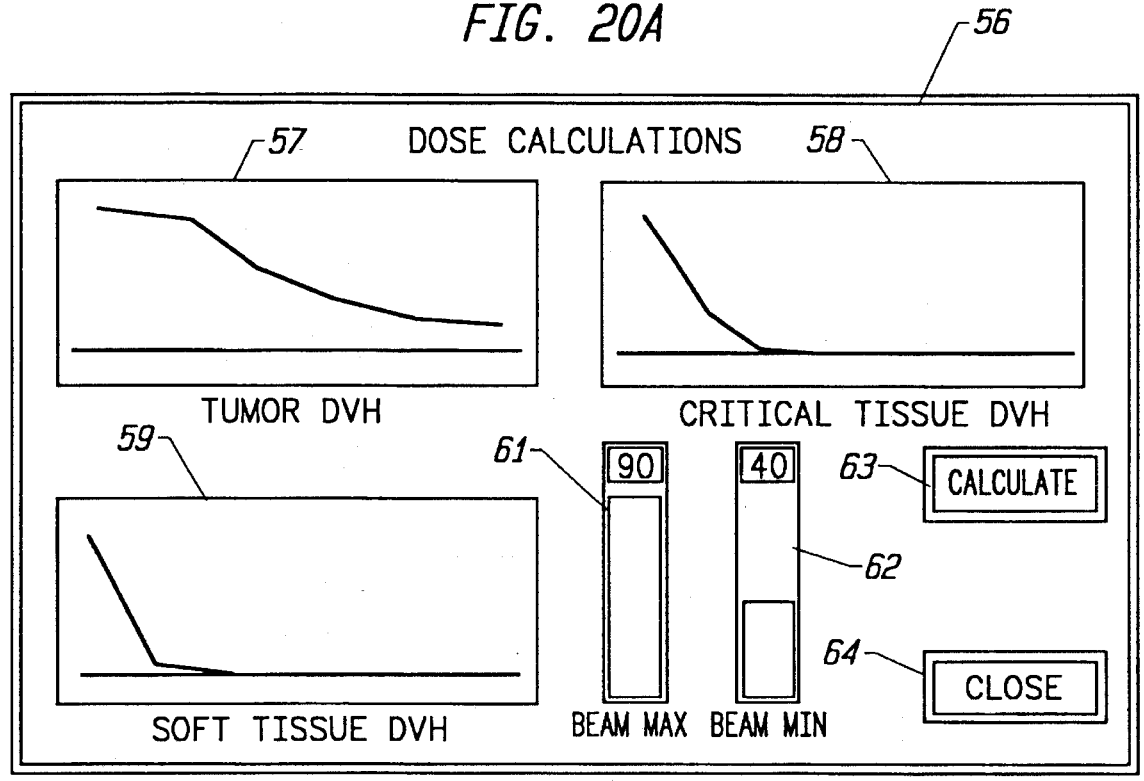

Referring to both the simplified scheme and the complex scheme, the interactability of the planner with the software program including the present invention is illustrated in FIGS. 20A and 20B. The computer display screen 51 shows the outline of a patient's head 52 having a tumor region 53 and a critical region 54 at the 16th slice as indicated at the bottom of screen 51. As discussed above, an appropriate dose is chosen for the tumor region while the lowest possible dose is chosen for the critical region. The dose for the soft tissue or healthy region surrounding both the tumor and critical regions is preferably as low as possible as well. Also showing on the computer display screen is the dose calculation display 56 which shows the graphed values for tumor dose volume histogram (DVH) 57, critical tissue DVH 58 and soft tissue DVH 59. The DVHs shows the volume (ordinate values) absorbing a dose x as a function of x (abscissa). The x axis is in dose percentages, such being 0% to 100%, and the y axis is in volume. Thus the graphs such show how much of the volume is receiving what dosage percentage level. Thus, DVH's are used to determine the homogeneity of a distribution.

In order to adjust the weighing values, adjustment manipulators 61 and 62 are provided. The beam weight for non-critical beams is adjusted by sliderbar 61 and the beam weight for critical beams is adjusted by sliderbar 62 when the calculation by function 62 is activated. Instead of two sliderbars one can use a separate sliderbar for each critical region. Finally, when the surgeon is satisfied with results provided by graphs 57, 58 and 59, the data can be saved by activating the close function 64.

Figure 21A:
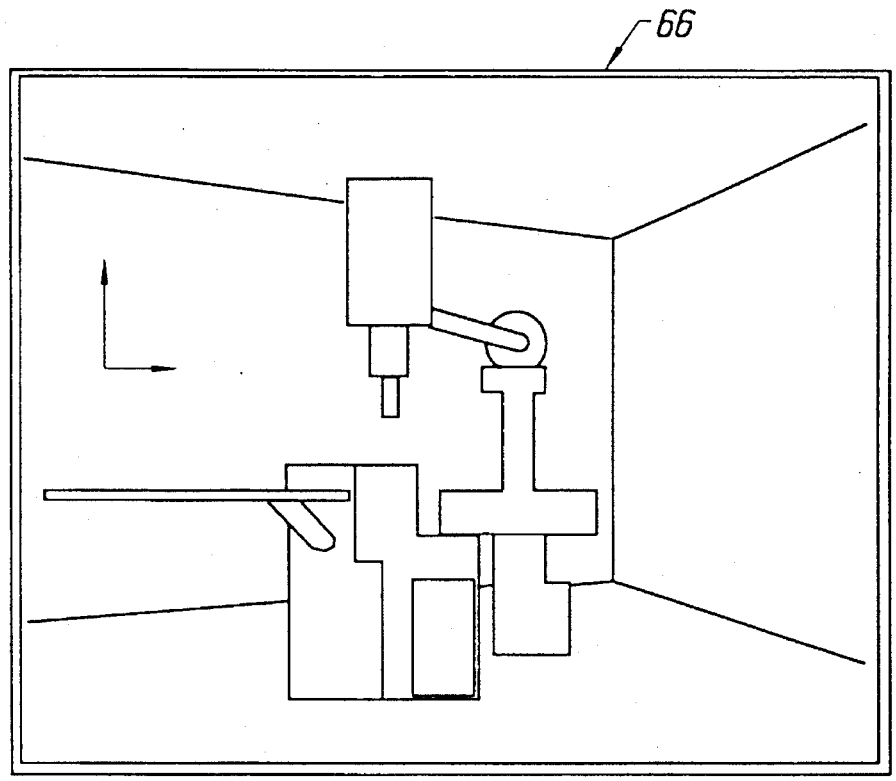
FIGS. 21A and 21B show the robotic arm and apparatus configuration and a motion path template according to the present invention.
Figure 21B:
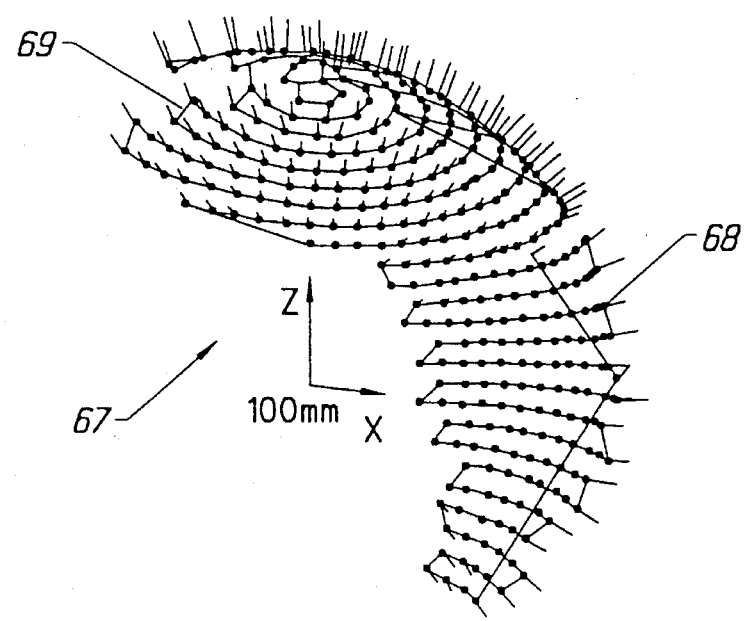

The beam configurations selected by the planning system and method of the present invention must be organized into a sequence defining a collision-free path of the radiation source. Referring to FIGS. 21A and 21B, the robotic arm and apparatus configuration is generally depicted as 66. As the arm moves about providing beams according to the planned beam configurations, there is the possibility that the arm could collide with other objects in the operating room such as sensors: moreover, the kinematics of the robotic arm has physical limitations as to its ability to be placed in particular positions. The treatment beams are selected in such a way that they are within angular limits given with a hand-coded precomputed motion template.

According to the present invention, a hard-coded sequence of beams, called nodes, is provided. A node 68 is given by a tool center point placement. In other words, the nodes provide a template of allowable points at which beams may be directed. Moreover, the lines 69 connecting the nodes 68 provide the order in which the beams are applied. The nodes 68 are generated by using tool center points on a sphere of appropriate radius centered at the origin.

For each node, a local joint space is computed. Thus, angle limits within which the arm and the accelerator can be moved without colliding or getting into the line of sight of a camera are associated with each node. To compute the treatment beam configurations given the particular tumor shape and location, the isocenter points are connected to the tool center points which are associated with the nodes. Thus each treatment beams is given by an isocenter point and the tool center point for a node. Given reasonable bounds for the tumor size, it can be assumed that the isocenter points are close to the workspace origin. Since the sourcetarget distance is large, it can be ensured that the angular deviation between a hard-coded node and associated treatment beam configuration remains below a fixed threshold, and within the local joint space of the node.

The placement of a cylinder beam in space is kinematically redundant. The beam can be translated along and rotated about its axis without changing spatial placement. Thus the beam has four degrees of freedom. The range of beam directions should be as large as possible to allow for homogeneous distributions. A simulating program is used to determine tool center points for nodes covering a large portion of half-spheres as shown in FIG. 21B. The beam widens with source-target distance. By placing tool center points for all nodes and treatment points on a sphere we can ensure that all beams have nearly constant and equal width in tissue.

Effector orientation is represented by three Euler angles such that the last of these angles gives the rotation about the beam central axis. For each node an appropriate value for this angle is computed with the work space simulator program. This value is chosen in such a way that arm posture changes along the path can be avoided.

The present invention provides a system which achieves better, faster, less painful, and more cost-effective treatment of brain tumors. Improvement in treatment quality is made possible by the versatile kinematics of the arm, the imaging system, and the treatment planning method and system. Faster treatment results from the use of computer-based tools to partially automate several fastidious processing steps. The treatment procedure for the new system is less painful since the stereotaxic frame is no longer needed. Cost-effectiveness results from a better use of the surgeon's time and a reduction of the treatment duration. The use of the present invention extends to other domains outside the brain such as prostate and lung cancers. Moreover, the present invention extends for tumors for which no treatment is currently available. In particular, this invention extends to very radiation-resistant tumors and cases in which conventional radiation therapy would cause too much damage to healthy tissue, and thus is not applicable.

FIG. 22 shows a photographic film phantom exposed for the example in FIGS. 2, 3 and 4, using the method of the present invention for selecting isocenter points. FIG. 22 (a-o) shows cross-sections taken along similar directions as the polygram in FIG. 2 starting at the bottom (a) and ending at the top (o). Thus, the shape of the region receiving high dose closely matches the input shape. Improved planning methods could include more constraints and perform a final optimization, i.e. an optimization over dose-volume histograms. The planning method and system of the present invention uses weighted arrangements in 3D. This is not limited to cylinders, and is appropriate for treatment planning in conventional radiation therapy as well. This therapy is the dominant treatment for cancer, and radiates a larger region around a tumor site from three to five directions with comparatively low dose.

The present invention further extends to stereolithography, rapid prototyping and 3D printing methods which are variants of a technique, where a moving laser beam is used to harden a liquid material in such a way that a particular shape is obtained, i.e. the laser beam is moved such that a region given by the desired input shape receives a high amount of energy, which the material in the surrounding shape remains liquid.

I claim:

1. A radiosurgery treatment planning method for simulating radiation treatment of tumorous tissue, comprising the steps of:

mapping a volume of tumorous tissue requiring irradiation and other regions to generate a model having a curvature;

distinguishing between tumorous tissue regions of said model requiring a predetermined dose of radiation and said other regions requiring less than said predetermined dose of radiation;

positioning at least several isocenter points in a distributed manner so that they can be superimposed upon said model of said mapped tumorous tissue requiring irradiation;

simulating radiation beams passing through said isocenter points; and determining which regions of said tumorous tissue received said predetermined dose of radiation by identifying first cells formed by crossing simulated radiation beams within said model of said tumorous tissue which, upon said simulating step, received a maximum number of radiation beams passing therethrough.

2. A method as recited in claim 1 further comprising the steps of:

identifying second cells formed by crossing simulated beams within said model of said tumorous tissue which, upon said simulating step, received a minimum number of radiation beams passing therethrough.

3. A method as recited in claim 2 further comprising the step of weighing said maximum and minimum radiation dose values.

4. A method as recited in claim 3 further comprising the steps of:

comparing said first cells with said model of said tumorous tissue;

determining whether said first cells and said model of said tumorous tissue occupy similarly shaped volumes.

5. A method as recited in claim 4 wherein in the event that said first cells and said model of said tumorous tissue do not occupy similarly shaped volumes, said method further comprising of repeating the method after and including said simulating step.

6. A method as recited in claim 3 further comprising the steps of:

comparing said second cells with said other regions requiring less than said predetermined dose of radiation; and determining whether said second cells and said other regions occupy similarly shaped volumes.

7. A method as recited in claim 1 wherein said mapping step includes the steps of providing CT scans of said volume of tumorous tissue requiring irradiation and its surrounding regions for graphic display as an image on a computer screen.

8. A method as recited in claim 7 wherein said mapping step further comprises the step of viewing said CT scan image in planar slices.

9. A method as recited in claim 8 wherein said distinguishing step includes the step of forming polygonal outlines at the circumference of said image representing said tumorous tissue.

10. A method as recited in claim 1 wherein said distinguishing step which includes distinguishing tumorous regions from other regions requiring less than said predetermined dose of radiation is performed in a manner which includes distinguishing tumorous regions from healthy tissue and critical regions.

11. A method as recited in claim 1 wherein said model has a surface and wherein said step of positioning isocenter points in a distributed manner includes imposing as a grid of points the surface of said model.

12. A method as recited in claim 1 wherein said positioning step includes imposing a line segment of points following the curvature of said model.

13. A radiosurgery treatment planning method for simulating radiation treatment of tumorous tissue, comprising the steps of:

mapping a volume of tumorous tissue requiring irradiation and other regions to generate a model;

distinguishing between tumorous tissue regions of said model requiring a predetermined dose of radiation and said other regions requiring less than said predetermined dose of radiation;

simulating radiation beams;

identifying first cells formed by simulating the crossing of said simulated radiation beams within said model of said tumorous tissue which, upon simulated treatment, receive a maximum number of radiation beams passing therethrough; and identifying second cells formed by crossing simulated radiation beams within said model of said tumorous tissue which, upon simulated treatment, received a minimum number of radiation beams passing therethrough.

14. A method as recited in claim 13 further comprising the step of weighing said maximum and minimum radiation dose radiation beam dosage values.

15. A method as recited in claim 14 further comprising the steps of:

comparing said first cells with said model of said tumorous tissue;

determining whether said first cells and said model of said tumorous tissue occupy similarly shaped volumes.

16. A method as recited in claim 15 further comprising the steps of:

comparing said second cells with said other regions requiring less than said predetermined dose of radiation; and determining whether said second cells and said other regions occupy similarly shaped volumes.

17. A radiosurgery treatment planning apparatus for simulating radiation treatment of tumorous tissue, comprising:

means for mapping a volume of tumorous tissue requiring irradiation and other regions to generate a model having a curvature;

means for distinguishing between tumorous tissue regions of said model requiring a predetermined dose of radiation and said other regions requiring less than said predetermined dose of radiation;

means for positioning at least several isocenter points in a distributed manner so that they can be superimposed upon said model of said mapped tumorous tissue requiring irradiation;

means for simulating radiation beams passing through said isocenter points; and means for determining which regions of said tumorous tissue received said predetermined dose of radiation through the identification of first cells formed by crossing simulated radiation beams within said model of said tumorous tissue which, upon said simulation of radiation beams, received a maximum number of simulated radiation beams passing therethrough.

18. An apparatus as recited in claim 17 further comprising:

means for identifying second cells formed by crossing simulated beams within said model of said tumorous tissue which, upon said simulating step, received a minimum number of radiation beams passing therethrough.

19. An apparatus as recited in claim 18 further comprising:

means for weighing said maximum and minimum radiation dose radiation beam dosage values.

20. An apparatus as recited in claim 19 further comprising:

means for comparing said first cells with said model of said tumorous tissue;

means for determining whether said first cells and said model of said tumorous tissue occupy similarly shaped volumes.

21. An apparatus as recited in claim 19 further comprising:

means for comparing said second cells with said other regions requiring less than said predetermined dose of radiation; and means determining whether said second cells and said other regions occupy similarly shaped volumes.

22. An apparatus as recited in claim 17 wherein said means for mapping includes means for providing CT scans of said volume of tumorous tissue requiring irradiation and its surrounding regions for graphic display as an image on a computer screen.

23. An apparatus as recited in claim 22 wherein said means for mapping further comprises means for viewing said CT scan image in planar slices.

24. An apparatus as recited in claim 23 wherein said means for distinguishing includes means for forming polygonal outlines at the circumference of said image representing said tumorous tissue.

25. An apparatus as recited in claim 17 wherein said means for distinguishing between tumorous regions of said model and other regions requiring less than said predetermined dose of radiation includes means for distinguishing between tumorous regions of said model and healthy tissue and critical regions.

26. An apparatus as recited in claim 17 wherein said model has a surface and said means for positioning includes means for imposing as a grid of points the surface of said model.

27. An apparatus as recited in claim 17 wherein said means for positioning said isocenter points in a distributed manner includes means for imposing a line segment of points or sequence of line segments following the curvature of said model.

28. A radiosurgery treatment planning apparatus for simulating radiation treatment of tumorous tissue, comprising:

means for mapping a volume of tumorous tissue requiring irradiation and other regions to generate a model;

means for distinguishing between tumorous tissue regions of said model requiring a predetermined dose of radiation and said other regions requiring less than said predetermined dose of radiation;

means for generating simulated radiation beams;

means for identifying first cells formed by crossing said simulated radiation beams within said model of said tumorous tissue which, upon simulated treatment, receive a maximum number of radiation beams passing therethrough; and means for identifying second cells formed by crossing simulated radiation beams within said model of said tumorous tissue which, upon simulated treatment, received a minimum number of radiation beams passing therethrough.

29. An apparatus as recited in claim 28 further comprising means for weighing said maximum and minimum radiation dose radiation beam dosage values.

30. An apparatus as recited in claim 29 further comprising:

means for comparing said first cells with said model of said tumorous tissue;

means for determining whether said first cells and said model of said tumorous tissue occupy similarly shaped volumes.

31. An apparatus as recited in claim 30 further comprising:

means for comparing said second cells with said other regions requiring less than said predetermined dose of radiation; and means for determining whether said second cells and said other regions occupy similarly shaped volumes.

* * * * *